United States Defensive Publication [19] (H) [11] T984,005

Lau [43] Jul. 3, 1979

[54] YELLOW-DYE-FORMING COUPLERS

[75] Inventor: Philip T. S. Lau, Rochester, N.Y.

[73] Assignee: Eastman Kodak Co., Rochester, N.Y.

[21] Appl. No.: 970,497

[22] Filed: Dec. 18, 1978

Related U.S. Application Data

[62] Division of Ser. No. 892,070, Mar. 31, 1978.

[51] Int. Cl.[2] ..... C07C 143/75

[52] U.S. Cl. ..... 260/401; 260/556 A; 260/556 S

[57] ABSTRACT

Novel bis yellow-dye-forming couplers are incorporated in photographic emulsions and elements. The couplers are represented by the structural formula

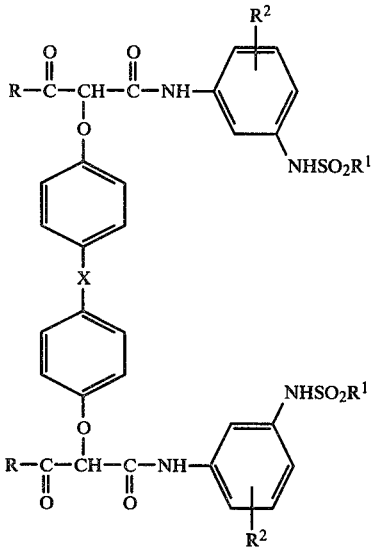

I where:

R is an aryl group of 6 to 12 carbon atoms, an aryloxyalkylene or arylthioalkylene group having 6 to 12 carbon atoms in the aryl portion of the group and 1 to 4 carbon atoms in the alkylene portion of the group, or an alkyl group of 1 to 8 carbon atoms;

$R^1$ is an alkyl group of 4 to 16 carbon atoms;

$R^2$ represents one or more halogen, lower alkyl, lower alkoxy, carboxy or lower alkoxycarbonyl substituents wherein the alkyl group and the alkyl portion of the alkoxy and alkoxycarbonyl groups contains 1 to 6 carbon atoms; and X is sulfonyl, carbonyl or alkylenedisulfonamido containing 1 to 4 carbon atoms.

5 Claims, No Sheets Drawing,

29 Pages Specification

The file of this unexamined application may be inspected and copies thereof may be purchased (849 O.G. 1221, Apr. 9, 1968).